United States Patent [19]

Hardy

[11] Patent Number: 4,981,686

[45] Date of Patent: Jan. 1, 1991

[54] PERSONAL LUBRICANT

[76] Inventor: Robert E. Hardy, 106 River Run, Greenwich, Conn. 06830

[21] Appl. No.: 241,061

[22] Filed: Sep. 6, 1988

Related U.S. Application Data

[63] Continuation of Ser. No. 50,861, May 18, 1987, abandoned.

[51] Int. Cl.$^5$ .................. A01N 63/00; A61K 37/00
[52] U.S. Cl. ........................ 424/93; 424/DIG. 14; 424/430; 514/873; 604/55; 252/52 R
[58] Field of Search ........... 252/52 R; 424/DIG. 14, 424/93, 430; 514/847, 873, 944, 947, 967, 969, 841, 843; 604/55, 285, 288

[56] References Cited

U.S. PATENT DOCUMENTS

| | | | |
|---|---|---|---|
| 3,953,599 | 4/1976 | Kilmer et al. | 514/947 |
| 4,021,578 | 5/1977 | Harich et al. | 514/969 |
| 4,411,893 | 10/1983 | Johnson et al. | 514/947 |
| 4,534,958 | 8/1985 | Adams et al. | 514/944 |
| 4,595,866 | 6/1986 | Flom | 514/873 |
| 4,627,934 | 12/1986 | Lindauer et al. | 424/195.1 |
| 4,670,256 | 6/1987 | Doran | 514/843 |
| 4,695,465 | 9/1987 | Kigasawa et al. | 514/947 |

Primary Examiner—Margaret B. Medley
Attorney, Agent, or Firm—Patrick J. Walsh

[57] ABSTRACT

A personal lubricant which is not contraceptive, does not impede sperm motility and may contain healing ingredients.

6 Claims, No Drawings

PERSONAL LUBRICANT

RELATED APPLICATION

This application is a continuation application of application Ser. No. 050,861, filed May 18, 1987, now abandoned.

The present invention is directed to a personal lubricant and in particular to a vaginal lubricant.

A lubricating fluid is normally present in the vagina and during sexual arousal an increased amount of the fluid is produced. The lack of sufficient vaginal lubrication causes vaginal tissue to become dry and irritated and may result in painful sexual intercourse and sometimes bleeding. There are a number of causes for this condition including decreased estrogen levels during menopause or after surgical removal of ovaries and after radiation therapy. Oral contraceptives and certain medications such as antihistaminics, antidepressants, blood pressure, and cardiac medicines can contribute to vaginal dryness. Additionally, psychological conditions including stress, fatigue and anxiety may impede production of the natural lubricant. A combination of hormonal and psychological factors may induce dryness temporarily after childbirth particularly if the mother is breastfeeding.

Common personal lubricants including K-Y Jelly and Vaseline are not ideal due to their consistency, poor lasting quality and lack of pleasant fragrance and acceptible taste. Those containing glycerin cause decreased sperm motility. Additionally, commercially available lubricants deal only with lubricating and do not contain ingredients that promote healing of vaginal tissue if irritation and inflammation are present.

Vaginal lubricating suppositories are sold commercially, however, they must be inserted into the mid-vagina to liquify adequately and then provide lubrication. There is a delay before the suppository melts when and where it is most needed.

Foam-type vaginal lubricants are also sold commercially. Some are packaged under pressure in containers similar to shaving cream cans. Their use has poor acceptibility because of the emission sound and they provide lubrication for only a relatively short time.

Occasionally insufficient natural vaginal lubrication is encountered in infertile couples during infertility investigations. Commercially available lubricants containing glycerin are spermicidal and impede sperm motility. Ingredients such as glycerin even in low concentrations have these disadvantages. Accordingly, such commercially available personal lubricants are not recommended for infertile couples where insufficient natural vaginal lubrication is troublesome.

SUMMARY OF THE INVENTION

The present invention is directed to a personal lubricant particularly a vaginal lubricant. The personal lubricant, according to the present invention, has a number of advantageous characteristics including lubricating ability, pleasant fragrance and taste, greaselessness, nonstaining, water solubility, nonirritating, humectant and harmless if ingested. Additionally, the vaginal lubricant soothes vaginal tissue. The lubricant does not prevent pregnancy and does not impede sperm motility and may be used when infertility is present.

In a preferred form the lubricant is available in cream form and may be used by either person.

A vaginal lubricant according to the present invention replaces natural lubrication and soothes irritated inflamed vaginal tissue when present. The lubricant is aesthetically acceptable in application and use, is applied externally to either partner, is nonspermicidal and does not impede sperm motility.

A preferred form of the invention includes one or more of petrolatum, coconut oil, anhydrous lanolin, mineral oil, egg albumen and stearyl alcohol as lubricants; aloe vera, lanolin, and allantoin as healing agents; sorbitol as a humectant and for taste; almond oil and coconut flavor as fragrances; propylparaben and methylparaben as preservatives; propylene glycol, water, stearyl alcohol, mineral oil; polyethylene gycol as solvents and sodium laurye sulfate as an emulsifier and wetting agent.

OBJECTS OF THE INVENTION

An object of the invention is to provide a personal lubricant for lubricating the vagina and for soothing vaginal tissue.

Another object of the invention is to provide a vaginal lubricant pleasing in fragrance and taste and being greaseless, nonstaining, water soluble, soothing and non-irritating.

Another object is to provide a vaginal lubricant which is non-spermicidal and does not impede sperm motility.

Another object is to provide a vaginal lubricant in cream form and useable by either person.

DETAILED DESCRIPTION OF THE INVENTION

A personal lubricant according to the invention includes one or more and preferably a combination of lubricants selected from petrolatum, coconut oil, anhydrous lanolin, mineral oil, egg albumen, and stearly alcohol. In addition to providing desired lubricity, these lubricants are consistent with other characteristics of the invention as being greaseless, non-staining, nonspermicidal, nonirritating and not impeding sperm motility, and in the case of lanolin being a healing agent. Other preferred ingredients for the lubricant include aloe vera and allantoin as healants, sorbitol as a humectant and for pleasing taste, and almond oil and coconut flavor as fragrances.

The following example illustrates a typical composition of the invention and is not intended to be limiting thereof.

| INGREDIENT | PERCENTAGE BY WEIGHT |
|---|---|
| Stearyl alcohol | 8.50 |
| Snow White Petrolatum | 5.00 |
| Lanolin Anhydrous | 8.00 |
| Sweet Almond Oil | 5.00 |
| Coconut Oil | 10.75 |
| Cetyl Alcohol | 0.50 |
| Mineral Oil (Drakeol #9) | 1.00 |
| Propylparaben | 0.09 |
| Water | 26.60 |
| Methylparaben | 0.15 |
| Sodium lauryl sulfate | 1.50 |
| Propylene Glycol | 3.00 |
| Aloe Vera Gel | 9.00 |
| Sorbitol | 1.00 |
| Allantoin | 2.50 |
| PEG 3350 | 14.00 |
| Egg Albumen | 2.50 |
| Coconut Flavor (P-5364 H. Kohnstamm) | 0.90 |

I claim:

1. A vaginal lubricant comprising as the lubricating ingredient, by weight, about 8.5% stearyl alcohol, 5% petrolatum, 8% anhydrous lanolin, 1% mineral oil, 2.5% egg albumin, and 10.75% coconut oil; and, by weight, about 44% solvents, about 11.5% healing agents, about 6% fragrances, about 1.5% emulsifier, about 1%, humectant, and about 0.25% preservatives.

2. A vaginal lubricant comprising in the approximate amount listed, the total being sufficient to amount to 100% by weight.

| | |
|---|---|
| Stearyl alcohol | 8.50 |
| Snow White Petrolatum | 5.00 |
| Lanolin Anhydrous | 8.00 |
| Sweet Almond Oil | 5.00 |
| Coconut Oil | 10.75 |
| Cetyl Alcohol | 0.50 |
| Mineral Oil | 1.00 |
| Propylparaben | 0.09 |
| Water | 26.60 |
| Methylparaben | 0.15 |
| Sodium lauryl sulfate | 1.50 |
| Propylene Glycol | 3.00 |
| Aloe Vera Gel | 9.00 |
| Sorbitol | 1.00 |
| Allantoin | 2.50 |
| PEG 3350 | 14.00 |
| Egg Albumen | 2.50 |
| Coconut Flavor | 0.90 |

3. A vaginal lubricant comprising a combination of lubricants in an amount which is effective to promote lubrication, comprising petrolatum, coconut oil, lanolin, mineral oil, egg albumin, and stearyl alcohol.

4. A vaginal lubricant of claim 3 which further includes aloe vera and allantoin as healant ingredients, in an amount which is effective to promote healing.

5. A vaginal lubricant according to claim 3 which further includes an amount of sorbitol which is effective to act as a humectant.

6. A vaginal lubricant of claim 3, 4 or 5 which further includes almond oil and coconut oil as fragrance ingredients in an amount which is effective to impart a fragrance.

* * * * *